US009724156B2

(12) United States Patent
Meymanat

(10) Patent No.: US 9,724,156 B2
(45) Date of Patent: Aug. 8, 2017

(54) SYSTEM FOR DETECTING, ACTIVELY TARGETING AND SELECTIVELY TREATING MALIGNANT CELLS IN HUMAN BODY BY NON-INVASIVE PROCEDURE

(71) Applicant: Mohammadreza Meymanat, Dolo (IT)

(72) Inventor: Mohammadreza Meymanat, Dolo (IT)

( * ) Notice: Subject to any disclaimer, the term of this patent is extended or adjusted under 35 U.S.C. 154(b) by 1035 days.

(21) Appl. No.: 13/945,776

(22) Filed: Jul. 18, 2013

(65) Prior Publication Data
US 2013/0310824 A1 Nov. 21, 2013

(51) Int. Cl.
*A61B 18/18* (2006.01)
*A61N 5/01* (2006.01)
*A61N 5/02* (2006.01)
*A61N 5/10* (2006.01)
*A61B 90/00* (2016.01)

(52) U.S. Cl.
CPC .............. *A61B 18/18* (2013.01); *A61N 5/01* (2013.01); *A61N 5/02* (2013.01); *A61N 5/025* (2013.01); *A61B 2090/3966* (2016.02); *A61N 2005/105* (2013.01)

(58) Field of Classification Search
CPC ............ A61B 18/18; A61B 2090/3966; A61N 2005/105; A61N 5/01; A61N 5/02; A61N 5/025; A61N 2/00; A61N 2/002; A61N 2/004; A61N 2/02; A61N 2/06; A61N 2/12
See application file for complete search history.

(56) References Cited

U.S. PATENT DOCUMENTS

| | | | | |
|---|---|---|---|---|
| 3,915,151 A | * | 10/1975 | Kraus | A61B 17/58 600/13 |
| 4,665,898 A | * | 5/1987 | Costa | A61N 2/02 600/14 |
| 5,667,469 A | * | 9/1997 | Zhang | A61N 2/12 600/9 |
| 5,788,624 A | * | 8/1998 | Lu | A61N 2/12 600/9 |
| D407,819 S | * | 4/1999 | Markoll | D24/183 |
| 2006/0100506 A1 | * | 5/2006 | Halperin | A61B 5/055 600/424 |
| 2008/0132785 A1 | * | 6/2008 | Piron | A61B 8/0825 600/426 |

(Continued)

*Primary Examiner* — Quynh-Nhu H Vu
(74) *Attorney, Agent, or Firm* — Barry Choobin; Patent 360

(57) ABSTRACT

The embodiments herein provide a system and method for detecting, actively targeting and selectively treating the biological targets in a human body by a non-invasive procedure. The system comprises an electromagnetic inductor supported at a predetermined height and rotated to generate a high frequency magnetic field. A head rest is provided at one end of a non-metallic bed provided at the center of the inductor for supporting a patient. A track is arranged below the bed to move the bed and the patient to a desired position indicated by a laser beam to efficiently aim at the targets. The electromagnetic inductor produces electric, magnetic and thermal effects on the nano-conductors attached to the biological targets to activate a nano drug infused into the blood stream of a patient and attached to the surface of the targets to dysfunction or destroy the targets.

9 Claims, 11 Drawing Sheets

(56) References Cited

U.S. PATENT DOCUMENTS

| | | | | |
|---|---|---|---|---|
| 2011/0054237 A1* | 3/2011 | Shapiro | ................. | A61B 5/411 |
| | | | | 600/12 |
| 2011/0172746 A1* | 7/2011 | Porter | ..................... | A61N 5/01 |
| | | | | 607/89 |
| 2011/0301497 A1* | 12/2011 | Shachar | ............. | A61B 1/00158 |
| | | | | 600/567 |
| 2013/0261368 A1* | 10/2013 | Schwartz | ............. | A61N 5/1027 |
| | | | | 600/1 |
| 2014/0029720 A1* | 1/2014 | Osherov | ................ | A61B 6/548 |
| | | | | 378/62 |
| 2014/0163664 A1* | 6/2014 | Goldsmith | ....... | A61B 17/00491 |
| | | | | 623/1.11 |
| 2016/0242849 A9* | 8/2016 | Crawford | ............. | A61B 17/025 |

\* cited by examiner

SYSTEM FOR DETECTING, ACTIVELY TARGETING AND SELECTIVELY TREATING MALIGNANT CELLS IN HUMAN BODY BY NON-INVASIVE PROCEDURE

CROSS-REFERENCE TO RELATED APPLICATION

This application claims priority to U.S. Provisional Application entitled, "Magnetic Active Nano Targeting," having Ser. No. 61/711,303, filed Oct. 9, 2012, which is entirely incorporated herein by reference.

SPONSORSHIP STATEMENT

The present invention is sponsored partially for international filing by Student Research Center, Zanjan University of Medical Science, Zanjan, Iran.

BACKGROUND

Technical Field

The embodiments herein generally relate to a medical device and particularly relate to a system and method for treating the patients affected with malignant cell borne diseases. The embodiments herein more particularly relate to a medical system and method for actively targeting and selectively treating the malignant cells using electrically, magnetically and thermally activated nano drug particles and an electromagnetic inductor.

Description of the Related Art

One of the greatest obstacles with cancer treatments is the ability to actively target and selectively treat only the malignant cells while leaving the normal cells unharmed. On the other hand, the major challenge in the cancer treatment is the ability to destroy the metastatic malignant cells early before a formation of a detectable tumor. In the past few years, many scientists have focused on the detection, targeting and selective treatment of malignant cells. Several methods developed in this issue have one or more demerits as discussed below.

A prior art method involves the use of cobalt spinel ferrite nano particles conjugated to a polypeptide specific for a receptor over expressed in ovarian cells. This prior art method demonstrated that the functionalized particles in a magnetic field could target and move metastatic cancer cells both in vitro and in vivo. In another prior art method, gold nano particles are used as biomarker detector in human fluid samples. Yet another prior art method involves exploiting the strong light scattering property of gold nano particles for developing the distinctive immunoassay probes. According to yet another prior art method, a Photo Thermal Therapy (PTT) was developed and electromagnetic radiation (most often in the form of infrared) was used to treat cancer. Many of the side effects and complications, as well as the potential applications of photo thermal therapy, are unknown. Still, a hyperthermia system for photo thermal cancer therapy was developed according to another prior art. An intravenous injection of this system followed by NIR laser irradiation to the tumor site resulted in an in vivo thermolysis. The standard and traditional treatments for cancer are carried out based on these methods. These methods are effective but they can produce a lot of damages to the normal cells. As an example, in chemotherapy, cytotoxic drugs are used. The cytotoxic drugs used in traditional treatment, can cause several serious side effects.

According to a prior art technique, the chemotherapy drugs are delivered to the cancer cells and heat is also applied to the cell. Researchers have used gold nanorods to which DNA strands are attached. The DNA strands act as a scaffold to hold the nanorod and the chemotherapy drug together. When the cancerous tumor is illuminated with infrared rays, the infrared rays are absorbed by gold nanorod and turned into heat. The heat releases the chemotherapy drug and helps to destroy the cancer cells. Though the abovementioned two prior arts provide a method to treat the tumors, the methods involve the use of cytotoxic drugs resulting in the generation of toxic and short or long term side effects to the patient.

According to another prior art, a targeted heat therapy is developed to destroy the tumors in case of breast cancer. In this method, the antibodies, which are strongly attracted to the proteins produced in one type of breast cancer cell, are attached to the nanotubes thereby causing the nanotubes to accumulate at the tumor. The infrared light from a laser is absorbed by the nanotubes to produce heat to incinerate the tumor.

According to yet another prior art, X-ray therapy is able to destroy the cancer tumors using a nanoparticle called nbtxr3. The nbtxr3 nanoparticles, which are attached to the cancer tumor, are activated by the X-rays to generate electrons to destroy the cancer tumors. This is intended to be used instead of radiation therapy to provide a lesser damage to the healthy tissue, but does not ensure a complete solution.

According to yet another prior art, an intriguing targeted chemotherapy method is used. The method involves using one nano particle to deliver the chemotherapy drug and another separate nano particle to guide the drug carrier to the tumor site. At first, the gold nanorods circulated through the bloodstream exit the point in which the blood vessels leak out in a cancer tumor site. Once the nanorods are accumulated at the tumor, they are used to concentrate the heat from infrared light at the tumor to heat up the tumor site. This heat increases the level of a stress in the proteins on the surface of the tumor. The drug carrying nano particle (a liposome) is attached to amino acids bound to this protein, so the increased level of protein at the tumor speeds up the accumulation of the chemotherapy drug carrying liposome at the tumor site.

According to yet another prior art, a photodynamic therapy is used. In the photodynamic therapy, the gene expression is manipulated using an UV light. However, the UV light may cause more harm than good to the patient. This method can cause a number of serious side effects such as surface damages. The UV light is unable to penetrate deep into the body and affect the deep seated tumors. It can cause serious damages to the normal tissues. On the other hand as it is discovered before, the UV light itself is carcinogenic.

According to yet another prior art, a way to control gene expression by using nano particles was discovered. In this method, the near-infrared (NIR) light is converted into visible or UV light. The nano particles can be introduced into target sites of the patient, to do their good work. The NIR, besides being non-toxic, is also able to penetrate deeper into our tissues (in comparison to normal UV photodynamic therapy). When the NIR reaches the desired places in the body of the patient, the nano particles, are able to convert the NIR back to UV light (up-conversion) to effectively activate the genes in the desired manner. The nano particles are also used to produce visible light and the application is extended to other light-based therapies. The conventional light therapy for treating tumors uses visible light to activate the light sensitive drugs that can kill cancer cells. However, such visible light is too penetrative to reach the deep-seated tumors.

According to yet another prior art, the radioactive particles or radiations are used for treating the malignant cells, but the radiation itself is found to be carcinogenic. Sometimes a treatment of one cancer through radioactive particles/radiations can cause another cancer which is more dangerous. This phenomenon is called secondary malignancy. As an example, the majorities of patients with Hodgkin lymphoma (HL) are able to achieve long-term survival and are freed of HL after treatment with radioactive radiations. But more complications are developed at later stage leading to a competing cause of death and morbidity. The long-term survivors are at a risk of being developed with secondary malignancies, cardiovascular disease such as due to anthracycline toxicity or mediastinal radiation, pulmonary disease such as due to radiation and/or bleomycin, thyroid dysfunction, and sterility, etc.

The use of nanotechnology in the cancer treatment offers some exciting possibilities, including the possibility of destroying the cancer tumors with a minimal damage to a healthy tissue and organs, the early detection and elimination of cancer cells before being formed into tumors. Further, the prior art method discloses the use of X-ray machines, Infra red, and UV lights for generating a heating effect at the site of malignant cells through the nano particle. But none of the prior art discusses about a treatment of malignant cells in the patient's body using an electromagnetic effect. Till now, the electromagnetic effect has been used only for various processes such as induction heating, induction welding, induction cooking, induction brazing, induction sealing, induction heating for fitting etc. These processes do not disclose the use of electromagnetic effect in the medical field.

Hence, there is a need for a safe, non hazardous and non invasive system and method for treating the malignant cancer/tumor cells in a human body. Also, there is need for a novel method, with minimum invasion, which enables to penetrate limitless inside the human cells and tissues for proper treatment. Further, there is need for a magnetic induction based method to enable the magnetic force and filed to penetrate deep inside the human cells and tissues without any limit for proper treatment. Still further, there is a need for using specific nano particles for treating only the malignant cells without affecting the healthy tissues. Still further, there is a need for a method and system for adopting a non cytotoxic drug based treatment procedure.

The abovementioned shortcomings, disadvantages and problems are addressed herein and which will be understood by reading and studying the following specification.

Objects of the Embodiments

The primary object of the embodiment herein is to provide a system for detecting, actively targeting and selectively treating a plurality of biological targets such as malignant cells by means of an extrinsic electromagnetic inductor and an intrinsic probe comprising a nano drug.

Another object of the embodiments herein is to provide a method for treating a malignant cell based disease in a human body using a non-toxic and non-invasive procedure.

Yet another object of the embodiments herein is to provide a method for infusing a plurality of intrinsic probes comprising metallic and/or non-metallic conductive nano particles into the human body for treating the targets selected from a group consisting of cells, biological molecules, endogen or exogenous proteins, toxins, viruses, bacteria, abnormal or malignant cells, malignant cell membrane, a bacterial cell wall, a yeast cell wall, a viral capsid and tissues.

Yet another object of the embodiment herein is to provide plurality of intrinsic probes in different shapes made from plurality of materials for yielding different combination of electrical, magnetic and thermal effect on a target.

Yet another object of the embodiment herein is to provide a system and method for activating the plurality of infused intrinsic probes inside the human body with an extrinsic electromagnetic inductor.

Yet another object of the embodiment herein is to provide a laser ray generator on the electromagnetic inductor system for indicating a location of strong magnetic lines of force for an effective destruction of the malignant cells.

Yet another object of the embodiment herein is to provide a method and system for treating not only the malignant cells but also a plurality of undesired biological elements inside the human body.

Yet another object of the embodiment herein is to provide a method and system for detecting and destroying micro metastasis and other malignant clusters/cells, and for preventing the building of a new tumor in other parts of the human body.

Yet another object of the embodiment herein is to provide a method and system for diagnosing an exact position of the malignant cells in the human body by using the suitable imaging technologies.

Yet another object of the embodiment herein is to provide a method and system to eliminate a toxic/undesired effect of the infused metallic nano drug by coating the metallic nano drug with a coating material.

Yet another object of the embodiment herein is to provide a method and system to eliminate the usage of the radioactive particles and procedures for treating the malignant cells in a human body.

These and other objects and advantages of the embodiments herein will become readily apparent from the following detailed description taken in conjunction with the accompanying drawings.

SUMMARY

The various embodiments herein provide a system for detecting, actively targeting and selectively treating the targets in a human body by a non-invasive procedure. The system comprises an electromagnetic inductor for generating a high frequency magnetic field, a base for supporting the electromagnetic inductor at a predetermined height, an electromotor for rotating the electromagnetic inductor around an axis at a point of support, a non metallic bed for supporting a patient under treatment, a head rest provided at one end of the non-metallic bed, a bed moving track arranged below the non-metallic bed for adjusting a position of the patient under treatment to a desired position and a laser ray generator for indicating a magnetic lines of force and an area in which a magnetic field density or magnetic flux is maximum. The laser generator enables an operator to aim at a target in a human body of the patient. The system further comprises a frequency inverter for adjusting a frequency of the magnetic field, an adjustable power generator for adjusting a magnetic flux of the high frequency magnetic field based on a requirement of a physician, and one or more air circulating fans for maintaining the electromagnetic inductor at a normal temperature by a continuous circulation of air. The electromagnetic inductor is an extrinsic system to produce electric, magnetic and thermal effects on an intrinsic probe placed in the target to activate a nano drug, which is infused into a blood stream of the patient and attached to a surface of the target to dysfunction or destroy the target. The target is selected from a group consisting of cells, biological molecules, endogen or exogenous proteins, toxins, viruses, bacteria, abnormal or malignant cells, malignant cell membrane, a bacterial cell wall, a yeast cell wall, a viral capsid and tissues.

According to an embodiment herein, the intrinsic probe is a conductive nano drug, comprising a nano conductor, a toxicity shield and a specific connector molecule. The nano conductor is formed in a shape of a nano structure. The nano structure is selected from a group consisting of a nano rod, a nano wire, a nano tube, a nano arc and a nano ring. The nano structure is a nano rod. The nano conductor is a metallic nano conductor. The nano rod is a gold nano rod. The toxicity shield is formed by coating Poly Ethylene Glycol (PEG) material over the nano conductor for preventing toxic effect of a conductor material or element. The specific connector molecule is used for attaching the nano conductor to the target in the human body of the patient.

According to an embodiment herein, the nano drug comprising the nano conductor is introduced inside a body of the patient by mixing the nano drug in a normal 0.9% NaCl saline solution to obtain a nano drug solution and by infusing the nano drug solution into a vein of the patient. The nano drug is circulated inside the body of the patient through blood vessels to attach the nano drug to a surface of the targets. A plurality of unattached nano drugs are expelled from the body of the patient through urine.

According to an embodiment herein, the electromagnetic inductor produces the high frequency magnetic field across the nano conductor in the nano drug, which is attached to the surface of the targets, and induces magnetic, electric and thermal effects in the nano conductor to activate the nano drug to cause a dysfunction or a destruction of the target. The nano drug causes a malfunctioning of the target and causes a dysfunction and a destruction of the target.

According to an embodiment herein, the electric, magnetic and thermal effects induced in the nano conductor depends on a size of the nano conductor and a frequency of a magnetic field. A direction and a magnitude of the magnetic field are changed continuously.

According to an embodiment herein, the electromagnetic inductor is designed in any one of an open U shape, a closed circular shape, and a rectangular shape. The electromagnetic inductor produces dense and parallel magnetic lines of force at a centre.

According to an embodiment herein, the laser beam projected by the laser ray generator is a planar laser beam. The laser ray generator projects the laser beam at a place with a maximum magnetic flux. The maximum magnetic flux is due to the high frequency magnetic field. A target area of the patient is positioned at a place of maximum magnetic flux by the movable bed track to provide an optimal treatment.

According to an embodiment herein, the intrinsic probe comprising metallic nano conductor has a radio opacity to visualize the target during an imaging process.

According to an embodiment herein, the intrinsic probe is activated remotely. The intrinsic probe is activated to present an electric field and a bipolar magnetic filed in a nano scale.

According to an embodiment herein, a method for detecting, actively targeting and selectively treating a target in a human body by a non-invasive procedure is provided. The method comprises the steps of infusing a nano drug comprising a nano conductor into a human body of a patient under treatment through a blood stream, circulating the nano conductor through a blood stream and attaching the nano conductor to a surface of a target in a human body of the patient, conducting a medical imaging procedure of the patient for identifying the target, marking and focusing an identified target area over the body of the patient using a laser beam, switching ON an electromagnetic inductor for generating a high frequency magnetic field for activating and functionalizing the nano conductor, inducing electric, magnetic and thermal effects in the nano conductor with the high frequency magnetic field generated by the electromagnetic inductor to destroy the target, removing the destroyed target and a plurality of used nano conductors through urine and recycling the urine for reusing the plurality of nano conductors.

According to an embodiment herein, a plurality of infused nano conductors which are not attached to the surface of the target is removed through the urine.

According to an embodiment herein, the target is treated out in a plurality of steps. The patient is hydrated before and after each step to reduce a burden of the kidneys.

According to an embodiment herein, the target is selected from a group consisting of cells, biological molecules, endogen or exogenous proteins, toxins, viruses, bacteria, abnormal or malignant cells, malignant cell membrane, a bacterial cell wall, a yeast cell wall, a viral capsid and tissues.

According to an embodiment herein, the nano drug is a conductive nano drug comprising a nano conductor, a toxicity shield and a specific connector molecule. The nano conductor is formed in a shape of a nano structure and the nano structure is selected from a group consisting of a nano rod, a nano wire, a nano tube, a nano arc and a nano ring. The nano structure is a nano rod and the nano conductor is a metallic nano conductor. The nano rod is a gold nano rod. The toxicity shield is formed by coating Poly Ethylene Glycol (PEG) material over the nano conductor for preventing toxic effect of a conductor material or element. The specific connector molecule is used for attaching the nano conductor to the target in the human body of the patient.

According to an embodiment herein, the nano drug comprising the nano conductor is infused inside a body of the patient by mixing the nano drug in a normal 0.9% NaCl saline solution to obtain a nano drug solution and by infusing the nano drug solution into a vein of the patient.

According to an embodiment herein, the electromagnetic inductor produces the high frequency magnetic field across the nano conductor in the nano drug, which is attached to the surface of the targets, and induces magnetic, electric and thermal effects in the nano conductor to activate the nano drug to cause a dysfunction or a destruction of the target. The nano drug causes a malfunctioning of the target and causes a dysfunction and a destruction of the target.

According to an embodiment herein, the electric, magnetic and thermal effects induced in the nano conductor depends on a size of the nano conductor and a frequency of a magnetic field. A direction and a magnitude of the magnetic field are changed continuously.

According to an embodiment herein, the laser beam is projected by the laser ray generator. The projected laser beam is a planar laser beam. The laser beam is projected at a place with a maximum magnetic flux and the maximum magnetic flux is due to the high frequency magnetic field. A target area of the patient is positioned at a place of maximum magnetic flux to provide an optimal treatment.

According to an embodiment herein, the nano drug comprising metallic nano conductor has a radio opacity to visualize the target during an imaging process.

According to an embodiment herein, the nano drug is an intrinsic probe and the intrinsic probe is activated remotely. The intrinsic probe is activated to present an electric field and a bipolar magnetic filed in a nano scale.

The various embodiments herein provide a system for detecting, actively targeting and selectively treating the malignant cells in a human body by a non-invasive procedure. The system comprises an electromagnetic inductor for generating a high frequency magnetic field, a base for supporting the electromagnetic inductor at a predetermined height, an electromotor for rotating the electromagnetic inductor around an axis at a point of support, a non metallic bed for supporting a patient under treatment, a head rest provided at one end of the non-metallic bed, a bed moving track arranged below the non-metallic bed for adjusting a position of the patient under treatment to a desired position, and a laser ray generator for indicating a magnetic lines of force and an area in which a magnetic field density or magnetic flux is maximum. The laser ray generator enables an operator to efficiently target a plurality of malignant cells of the patient.

The system further comprises a frequency inverter for adjusting a frequency of the high current producing magnetic field, a power generator for generating high current and low voltage, an adjustable power generator for adjusting a magnetic flux of the high frequency magnetic field based on a requirement of a physician, one or more air circulating fans for maintaining the electromagnetic inductor at a normal temperature by a continuous circulation of air. The electromagnetic inductor is an extrinsic system to produce electric, magnetic and thermal effect on an intrinsic probe placed in the plurality of malignant cells to activate a nano drug infused into the plurality of the malignant cells to dysfunction or destroy the plurality of malignant cells.

According to an embodiment herein, the intrinsic probe is a metallic nano drug, comprising a metallic nano drug particle. The metallic nano drug particle is formed in a shape of a nano structure. The nano structure is selected from a group consisting of a nano rod, a nano wire, a nano tube, a nano arc and a nano ring. The nano structure is a nano rod. The nano rod is a gold nano rod. A material for the nano structure is selected from a group of materials comprising conductive materials such as metals like gold. The intrinsic probe further comprises a toxicity shield. The toxicity shield is formed by coating Poly Ethylene Glycol (PEG) material over the metallic nano drug particle for preventing toxic effect or undesired effect of a metallic element. Still further, the intrinsic probe comprises a specific connector molecule for attaching the metallic nano drug particle to the malignant cells.

According to an embodiment herein, the nano drug comprising gold nanorods are introduced inside a body of the patient by mixing the nano drug in a normal 0.9% NaCl saline solution to obtain a nano drug solution and by infusing the nano drug solution into a vein of the patient. The nano drug is circulated inside the body of the patient through the blood vessels to attach the nano drug particles to one or more target organs affected with the malignant cells. A plurality of unattached nano drug particles is expelled from the body of the patient through urine.

According to an embodiment herein, the electromagnetic inductor produces the high frequency magnetic field across the nanorods which are attached to the malignant cells and induces magnetic, electric and thermal effect in the nanorods to activate the metallic nano drug to cause a dysfunction or a destruction of the malignant cells. The nanorods malfunctions the target malignant cells and causes dysfunction and destruction. The malignant cell is selected from a group consisting of a malignant cell membrane, a bacterial cell wall, a yeast cell wall, and a viral capsid.

According to an embodiment herein, the electric, magnetic and thermal effect induced in the nanorod depends on a size of the nanorod and a frequency of a magnetic field. A direction and a magnitude of the magnetic field are changed continuously.

According to an embodiment herein, the electromagnetic inductor is designed in any one of an open U shape, a close circular shape, and a rectangular shape. The electromagnetic inductor produces dense and parallel magnetic lines of force at a center.

According to an embodiment herein, the laser beam projected by the laser ray generator is a planar laser beam. The laser ray generator projects the laser beam at a place with a maximum magnetic flux. The maximum magnetic flux is due to the high frequency magnetic field. A malignant cell area of the patient is positioned at the place of maximum magnetic flux by the movable bed track to provide an optimal treatment.

According to an embodiment herein, the intrinsic system comprising gold nanorods has high radio opacity to visualize a target malignant cell during an imaging process.

According to an embodiment herein, the metallic nano drug is a gold nanorod coated with polyethylene glycol. The metallic nano drug is glutaraldehyde.

According to an embodiment herein, a method for detecting, actively targeting and selectively treating malignant cells in a human body by a non-invasive procedure is provided. The method comprises, infusing a nano drug comprising a plurality of gold nanorods into a body of a patient, circulating the plurality of gold nanorods in a blood stream and attaching the plurality of gold nanorods to a plurality of malignant cells and malignant tissues in a target organ, conducting a medical imaging procedure of the patient for identifying the plurality of malignant cells, marking an identified malignant cells area over the body of the patient, switching ON an electromagnetic inductor for activating and functionalizing the plurality of gold nanorods, inducing electric, magnetic and thermal effect in the plurality of gold nanorods by rotating the electromagnetic inductor to destroy the malignant cells and tissues in the target area, filtering the destroyed malignant cells and tissues along with a plurality of used gold nanorods through kidney, removing the destroyed malignant cells through a urine, and recycling the urine for reusing the plurality of gold nanorods.

According to an embodiment herein, the plurality of infused gold nanorods which are not attached with a plurality of malignant cells are filtered through the kidneys and is removed through the urine.

According to an embodiment herein, the plurality of malignant cells is treated out in a plurality of steps. The patient is hydrated before and after each step to reduce a burden of the kidneys in filtering the destroyed malignant cells and used nanorods.

According to an embodiment herein, the method and system is used for treating a number of biologic materials/factors including malignant cells. The biologic materials/factors are not only limited to the malignant cells but also include every biological molecules, endogen or exogenous proteins, toxins, viruses, bacteria, abnormal or malignant cells and tissues. The biologic materials/factors are also termed as "targets".

According to an embodiment herein, the nano drug comprising the nano rods are not only used in medical filed but also used as a nano probe in electronics and electrical fields. Further, the nano rod is a nano scale pill or nano drug or nano probe which is remotely activated. Each nano probe provides an electrical field or bipolar magnetic fields in a nano scale. The bipolar nano particles have biological and electrical functions in nano scale, which are used in electronics industry.

According to an embodiment herein, the nano conductors are made up of a plurality of metallic and/or non-metallic conductive materials in different shapes. A combination of magnetic, electric and thermal effects produced by a conductor material is dependent on a conductor material. The combination of magnetic, electric and thermal effects produced by a conductor material is different for different conductor materials. Each conductive material has a specific effect on the target. The effect of individual conductor material is practically realized or obtained by performing several experiments. Similarly, an optimal conductive or conductor material along with an optimum size is found for each target after several experiments.

According to an embodiment herein, the conductive material is a metallic conductive material and the metallic conductive material is gold and the metallic conductor is a gold nano rod.

According to an embodiment herein, the nano drug comprising a plurality of nano conductor materials is infused into a blood stream of a patient and the nano drug is attached to the surface of the targets or malignant cells or any other biological target factors.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
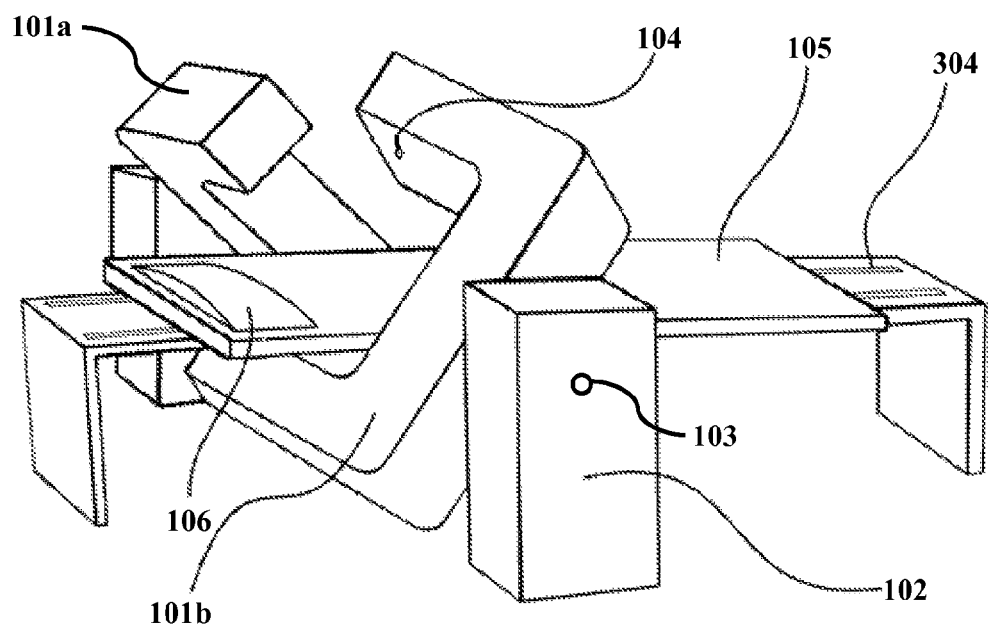
FIG. 1 illustrates a side perspective view of a system comprising two U-shaped electromagnetic inductors for activating the gold nano drug particles, according to an embodiment herein.

Although the specific features of the embodiments herein, are shown in some drawings and not in others. This is done for convenience only as each feature may be combined with any or all of the other features in accordance with the embodiments herein.

DETAILED DESCRIPTION OF THE DRAWINGS

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a system for detecting, actively targeting and selectively treating the malignant cells in a human body by a non-invasive procedure. The system comprises an electromagnetic inductor for generating a high frequency magnetic field, a base for supporting the electromagnetic inductor at a predetermined height, an electromotor for rotating the electromagnetic inductor around an axis at a point of support, a non metallic bed for supporting a patient under treatment, a head rest provided at one end of the non-metallic bed, a bed moving track arranged below the non-metallic bed for adjusting a position of the patient under treatment to a desired position, and a laser ray generator for indicating a magnetic lines of force and an area in which a magnetic field density or magnetic flux is maximum. The laser ray generator enables an operator to efficiently target a plurality of malignant cells of the patient.

The system further comprises a frequency inverter for adjusting a frequency of the high current producing magnetic field, a power generator for generating high current and low voltage, an adjustable power generator for adjusting a magnetic flux of the high frequency magnetic field based on a requirement of a physician, one or more air circulating fans for maintaining the electromagnetic inductor at a normal temperature by a continuous circulation of air. The electromagnetic inductor is an extrinsic system to produce electric, magnetic and thermal effect on an intrinsic probe placed in the plurality of malignant cells to activate a nano drug infused into the plurality of the malignant cells to dysfunction or destroy the plurality of malignant cells.

According to an embodiment herein, the intrinsic probe is a metallic nano drug, comprising a metallic nano drug particle. The metallic nano drug particle is formed in a shape of a nano structure. The nano structure is selected from a group consisting of a nano rod, a nano wire, a nano tube, a nano arc and a nano ring. The nano structure is a nano rod. The nano rod is a gold nano rod. A material for the nano structure is selected from a group of materials comprising conductive materials such as metals like gold. The intrinsic probe further comprises a toxicity shield. The toxicity shield is formed by coating Poly Ethylene Glycol (PEG) material over the metallic nano drug particle for preventing toxic effect or undesired effect of a metallic element. Still further, the intrinsic probe comprises a specific connector molecule for attaching the metallic nano drug particle to the malignant cells.

According to an embodiment herein, the nano drug comprising gold nanorods are introduced inside a body of the patient by mixing the nano drug in a normal 0.9% NaCl saline solution to obtain a nano drug solution and by infusing the nano drug solution into a vein of the patient. The nano drug is circulated inside the body of the patient through the blood vessels to attach the nano drug particles to one or more target organs affected with the malignant cells. A plurality of unattached nano drug particles is expelled from the body of the patient through urine.

According to an embodiment herein, the electromagnetic inductor produces the high frequency magnetic field across the nanorods which are attached to the malignant cells and induces magnetic, electric and thermal effect in the nanorods to activate the metallic nano drug to cause a dysfunction or a destruction of the malignant cells. The nanorods malfunctions the target malignant cells and causes dysfunction and destruction. The malignant cell is selected from a group consisting of a malignant cell membrane, a bacterial cell wall, a yeast cell wall, and a viral capsid.

According to an embodiment herein, the electric, magnetic and thermal effect induced in the nanorod depends on a size of the nanorod and a frequency of a magnetic field. A direction and a magnitude of the magnetic field are changed continuously.

According to an embodiment herein, the electromagnetic inductor is designed in any one of an open U shape, a close circular shape, and a rectangular shape. The electromagnetic inductor produces dense and parallel magnetic lines of force at a center.

According to an embodiment herein, the laser beam projected by the laser ray generator is a planar laser beam. The laser ray generator projects the laser beam at a place with a maximum magnetic flux. The maximum magnetic flux is due to the high frequency magnetic field. A malignant cell area of the patient is positioned at the place of maximum magnetic flux by the movable bed track to provide an optimal treatment.

According to an embodiment herein, the intrinsic system comprising gold nanorods has high radio opacity to visualize a target malignant cell during an imaging process.

According to an embodiment herein, the metallic nano drug is a gold nano rod coated with polyethylene glycol. The metallic nano drug is glutaraldehyde.

According to an embodiment herein, a method for detecting, actively targeting and selectively treating malignant cells in a human body by a non-invasive procedure is provided. The method comprises, infusing a nano drug comprising a plurality of gold nanorods into a body of a patient, circulating the plurality of gold nanorods in a blood stream and attaching the plurality of gold nanorods to a plurality of malignant cells and malignant tissues in a target organ, conducting a medical imaging procedure of the patient for identifying the plurality of malignant cells, marking an identified malignant cells area over the body of the patient, switching ON an electromagnetic inductor for activating and functionalizing the plurality of gold nanorods, inducing electric, magnetic and thermal effect in the plurality of gold nanorods by rotating the electromagnetic inductor to destroy the malignant cells and tissues in the target area, filtering the destroyed malignant cells and tissues along with a plurality of used gold nanorods through kidney, removing the destroyed malignant cells through a urine, and recycling the urine for reusing the plurality of gold nanorods.

According to an embodiment herein, the plurality of infused gold nanorods which are not attached with a plurality of malignant cells are filtered through the kidneys and is removed through the urine.

According to an embodiment herein, the plurality of malignant cells is treated out in a plurality of steps. The patient is hydrated before and after each step to reduce a burden of the kidneys in filtering the destroyed malignant cells and used nanorods.

According to an embodiment herein, the method and system is used for treating a number of biologic materials/factors including malignant cells. The biologic materials/factors are not only limited to the malignant cells but also include every biological molecules, endogen or exogenous proteins, toxins, viruses, bacteria, abnormal or malignant cells and tissues. The biologic materials/factors are also termed as "targets".

According to an embodiment herein, the nano drug comprising the nano rods are not only used in medical filed but also used as a nano probe in electronics and electrical fields. Further, the nano rod is a nano scale pill or nano drug or nano probe which is remotely activated. Each nano probe provides an electrical field or bipolar magnetic fields in a nano scale. The bipolar nano particles have biological and electrical functions in nano scale, which are used in electronics industry.

According to an embodiment herein, the nano conductors are made up of a plurality of metallic and/or non-metallic conductive materials in different shapes. A combination of magnetic, electric and thermal effects produced by a conductor material is dependent on a conductor material. The combination of magnetic, electric and thermal effects produced by a conductor material is different for different conductor materials. Each conductive material has a specific effect on the target. The effect of individual conductor material is practically realized or obtained by performing several experiments. Similarly, an optimal conductive or conductor material along with an optimum size is found for each target after several experiments.

According to an embodiment herein, the conductive material is a metallic conductive material and the metallic conductive material is gold and the metallic conductor is a gold nano rod.

According to an embodiment herein, the nano drug comprising a plurality of nano conductor materials is infused into a blood stream of a patient and the nano drug is attached to the surface of the targets or malignant cells or any other biological target factors.

FIG. 1 illustrates a side perspective view of a U shape electromagnet inductor for activating the gold nano drug particles, according to an embodiment herein. The electromagnetic inductor comprises two U shaped electromagnetic inductor arms 101*a* and 101*b* for producing a high frequency magnetic field or magnetic lines of force. The required frequency and the magnetic lines of force are produced as per the advice of a specialist doctor such as an oncologist. The two U shaped electromagnetic arms 101*a* and 101*b* are supported on two respective support posts 102. The U shaped electromagnetic arm 101*a* is mounted to the support post (not shown) at a support point (not shown). Similarly, the electromagnetic arm 101*b* is mounted to respective support post 102 at a respective support point 103. On mounting the electromagnetic arms 101*a* and 101*b* to the respective support posts at the support points, both the electromagnetic arms 101*a* and 101*b* are aligned in a common rotational axis. Alternately, the electromagnetic arms 101*a* and 101*b* are rotated at different rotational axes. The system is provided with and without an electromotor for rotating the electromagnetic inductor. An electromotor is provided to rotate the U shaped electromagnetic arms 101*a* and 101*b* at each of the support posts and at the respective support points. Similarly, another electromotor is provided for the U shaped electromagnetic arm 101*a*. The electromotor is either internally or externally mounted to the support post 102 at the support point 103 for the U shaped electromagnetic arm 101*b*. A laser ray generator 104 is also provided in at least one of the two U shaped electromagnetic arms 101*a* and 101*b*. The laser ray generator 104 projects or emits a point or planar laser beam for guiding an operator to treat a patient optimally. A non metallic bed 105 is provided with a head rest 106 along the central axis of the two U shaped electromagnetic arms 101*a* and 101*b*. The patient under treatment lies on the non metallic bed 105 and rests his/her head over the head rest 106 for comfort. The position of the patient is adjusted by changing the position of the non metallic bed 105 over a bed moving track (304). When an inductor with a closed shape, such as rectangular or circular inductor is selected, only one inductor is preferred or used to induce magnetic, electrical or thermal effects on the nano drug efficiently. When an inductor with an open shape, such as U-shaped inductor is selected, two U-shaped inductors are used to induce magnetic, electrical or thermal effects on the nano drug efficiently.

Figure 2:
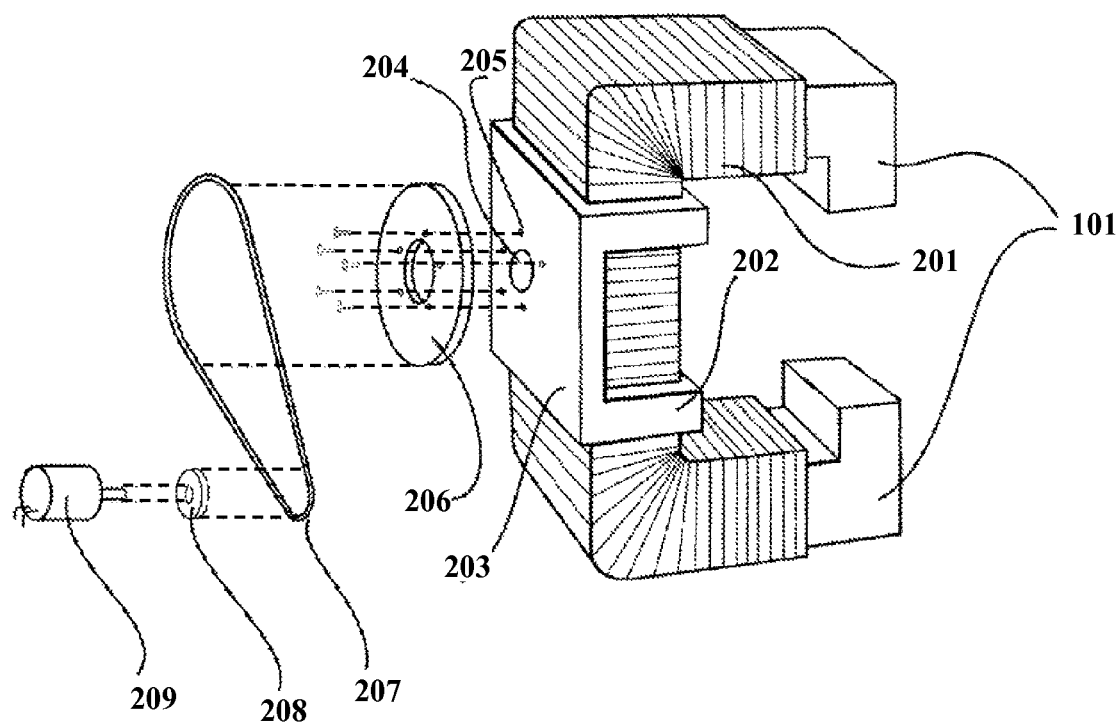
FIG. 2 illustrates an exploded perspective view of a U shaped electromagnetic inductor arm for activating the gold nano drug particle, according to an embodiment herein.

FIG. 2 illustrates an exploded perspective view of one U-shaped electromagnet inductor arm for activating the gold nano drug particle, according to an embodiment herein. The U-shaped electromagnetic inductor arm 101 with two pole terminals is shown. The electromagnetic inductor arm 101 comprises a ferrite core for providing a high permeability to the magnetic lines of force. The electromagnetic inductor arm 101 is wound with one or more coils 201 of conducting wire for producing the magnetic field by passing an Alternating Current (AC) through the coils 201. A high frequency alternative current is needed for the inductor to produce the high frequency alternative magnetic field. The electromagnetic inductor arm 101 is fixed with a holder arm 202 for providing a support for holding at a required or desired height. The top surface of the holder arm 202 is provided with a holder plate 203. The holder arm 202 and the holder plate 203 are preferably made of but not limited to Aluminum. The holder plate 203 is centrally holed to form an axial hole 204 with a predetermined depth and diameter. The U-shaped electromagnetic inductor arm 101 is mounted on a support post with a support point passing through the axial hole 204. The holder plate is further provided with a first pulley 206. The first pulley 206 is bolted to the holder plate through a series of pin holes 205 arranged around the axial hole 204. The first pulley 206 is coupled to a second pulley 208 through a belt 207. The second pulley 208 is coupled to an electromotor 209. The rotational energy from the electromotor 209 is transferred from the second pulley 208 to the first pulley 206 through the belt 207 which in turn rotates the coupled U-shaped electromagnetic inductor arm 101. The electromagnetic inductor arm 101 is rotated around the axis formed at the axial hole 204. The electromotor 209 is designed to spin the electromagnetic inductor 101 on the axis. A similar construction is adopted for a second electromagnetic inductor arm. The second electromagnetic inductor arm is mounted to a second post at a second support point. Both the electromagnetic inductor arms constitute electromagnetic inductor.

Figure 3:
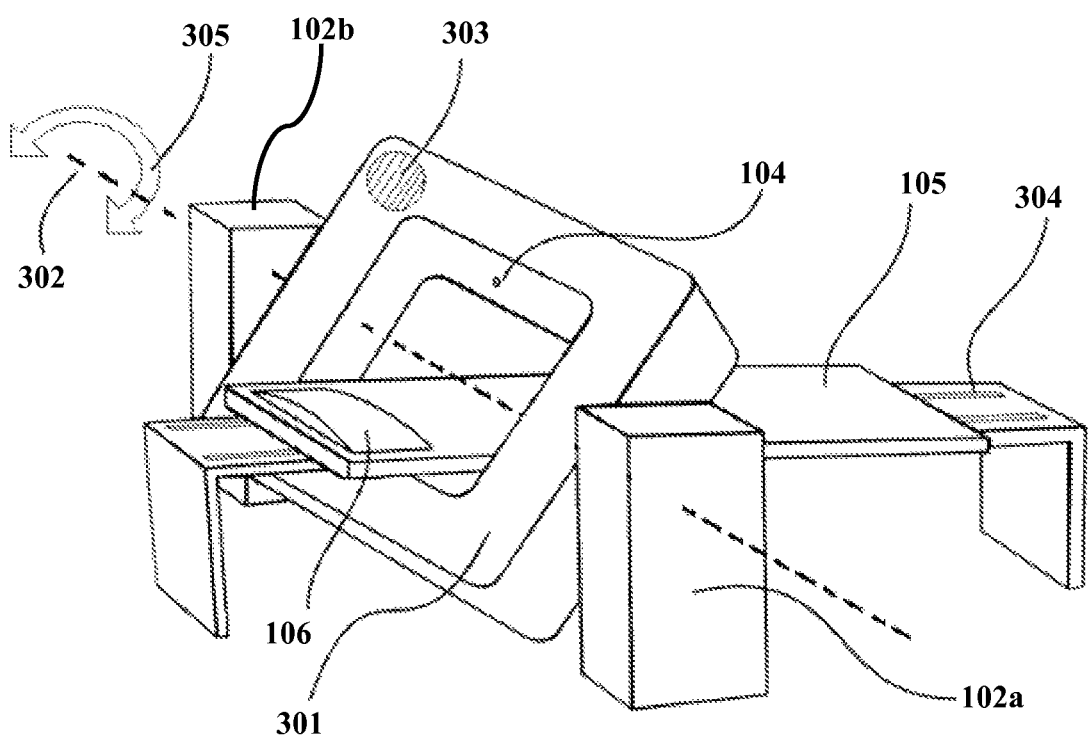
FIG. 3 illustrates a perspective view of a rectangular electromagnetic inductor for activating the gold nano drug particle, according to an embodiment herein.

FIG. 3 illustrates a perspective view of the rectangular electromagnetic inductor for activating the gold nano drug particle, according to an embodiment herein. The electromagnetic inductor assembly comprises a rectangular electromagnetic inductor 301 for producing a high frequency magnetic field or magnetic lines of force. The required frequency and the magnetic lines of force are produced as per the advice of a specialist doctor such as an oncologist. The electromagnetic inductor 301 is supported on two respective support posts 102*a* and 102*b*. The electromagnetic inductor 301 is fixed to the support post 102*a* and 102*b* at the respective support points on a rotational axis 302. An electromotor (not shown) is mounted at one of the support posts to rotate the electromagnetic inductor 301 about the rotational axis 302. The electromotor is able to rotate the electromagnetic inductor 301 in a clockwise direction or in an anticlockwise direction in steps as shown by the bidirectional arrow 305 around the rotational axis 302. The electromotor is either internally or externally mounted to the support post 102*a* or 102*b* at the respective support points. A laser ray generator 104 is provided at the inner periphery of the rectangular electromagnetic inductor 301. The laser ray generator 104 projects or emits a point or planar laser beam for guiding an operator to treat a patient optimally. The electromagnetic inductor 301 is also provided with one or more air circulating fans 303. The air circulating fans 303 prevent an increase in temperature and maintain a normal temperature around the electromagnetic inductor 301. A non metallic bed 105 with a head rest 106 is provided at the center of the electromagnetic inductor 301. The non metallic bed 105 is supported by a bed moving track 304. The patient under treatment lies down on the non metallic bed 105 and rests his/her head over the head rest 106 for comfort. The position of the patient is adjusted by changing the position of the non metallic bed 105 over the bed moving track 304.

Figure 4:
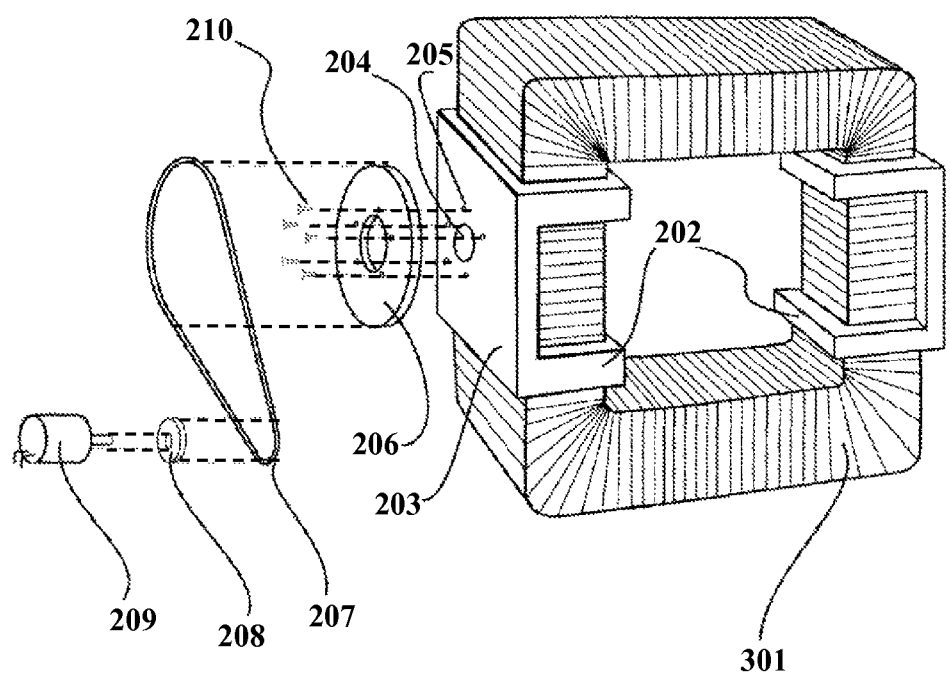
FIG. 4 illustrates an exploded perspective view of system comprising a rectangular electromagnetic inductor for activating the gold nano drug particle, according to an embodiment herein.

FIG. 4 illustrates an exploded perspective view of a rectangular electromagnetic inductor assembly for activating the gold nano drug particle, according to an embodiment herein. A rectangular electromagnetic inductor 301 with a coil of a conducting wire is wound on the entire surface. The electromagnetic inductor 301 is provided with a ferrite core for providing a high permeability to the magnetic lines of force. The electromagnetic inductor 301 is wound with one or more coils of conducting wire for producing the magnetic field. The magnetic field is generated by passing a high frequency Alternating Current (AC) through the coil of conducting wire. The electromagnetic inductor 301 is fixed with two holder arms 202. The two holder arms 202 provide a support for holding the electromagnetic inductor 301 at a predetermined height. The top surface of the two holder arms 202 is provided with a holder plate 203. The two holder arms 202 and the respective holder plates 203 are preferably made of but not limited to Aluminum. A central hole provided at both the holder plates 203 act as an axial hole 204 with a predetermined depth and diameter. The electromagnetic inductor 301 is mounted to a support post at a support point through the axial hole 204. The holder plate 203 is further firmly mounted with a first pulley 206 by bolting a plurality of pins 210 through a series of pin holes 205 around the axial hole 204. The first pulley 206 is coupled to a second pulley 208 through a belt 207. The second pulley 208 is coupled to an electromotor 209. The rotational energy from the electromotor 209 is transferred from the second pulley 208 to the first pulley 206 through the belt 207 which in turn rotates the electromagnetic inductor 301. The electromagnetic inductor 301 is rotated around the axis formed at the axial hole 204. The electromotor 209 is designed to spin the electromagnetic inductor 301 on the axis.

Figure 5:
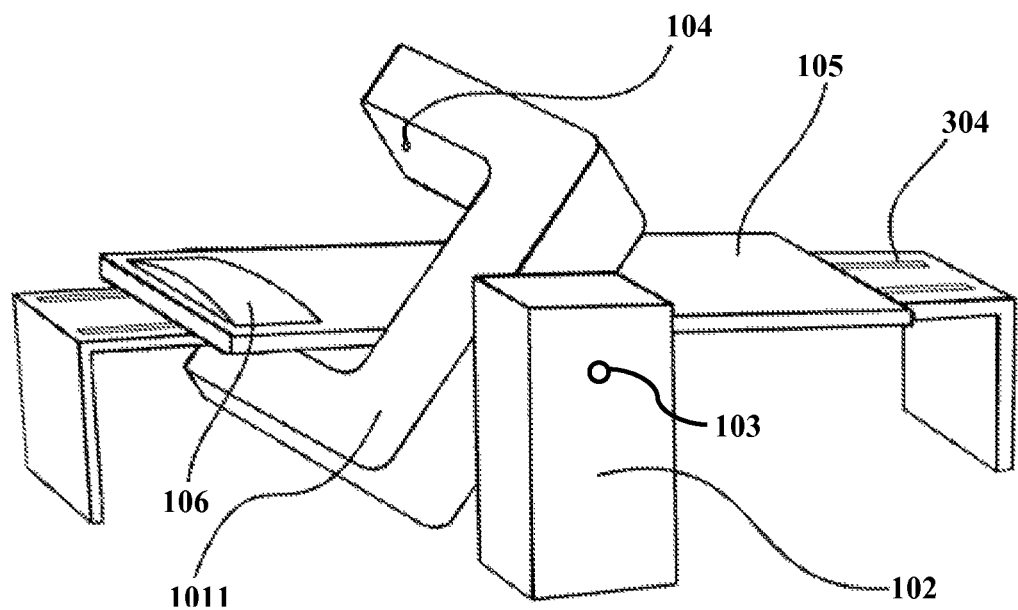
FIG. 5 illustrates a side perspective view of a system comprising a single U shaped electromagnetic inductor for activating the gold nano drug particles, according to an embodiment herein.

FIG. 5 illustrates a side perspective view of a single U shaped electromagnetic inductor for activating the gold nano drug particles, according to an embodiment herein. The electromagnetic inductor comprises one U shaped electromagnetic inductor arm 1011 for producing a high frequency magnetic field or magnetic lines of force. The required frequency and the magnetic lines of force are produced as per the advice of a specialist doctor such as an oncologist. The U shaped electromagnetic arm 1011 is supported on a support post 102 at a respective support point 103. An electromotor is provided to rotate the U shaped electromagnetic arm 1011 at the support post 102. The electromotor is either internally or externally mounted to the support post 102 at the support point 103 for the U shaped electromagnetic arm 1011. A laser ray generator 104 is also provided in the U shaped electromagnetic arm 1011. The laser ray generator 104 projects or emits a point or planar laser beam for guiding an operator to target a treatment area or to aim a biological target in the human body of a patient to treat the patient optimally. A non metallic bed 105 is provided with a head rest 106 along the central axis of the U shaped electromagnetic arm 1011. The patient under treatment lies on the non metallic bed 105 and rests his/her head over the head rest 106 for comfort. The position of the patient is adjusted by changing the position of the non metallic bed 105 over a bed moving track (304).

According to an embodiment herein, a rotator system for the inductor is essential only when a single U shaped inductor is used. But, no rotator system is required or the rotator system is used optionally, when two inductors are used. A system with only one U shaped inductor is easier to handle and operate.

Figure 6:
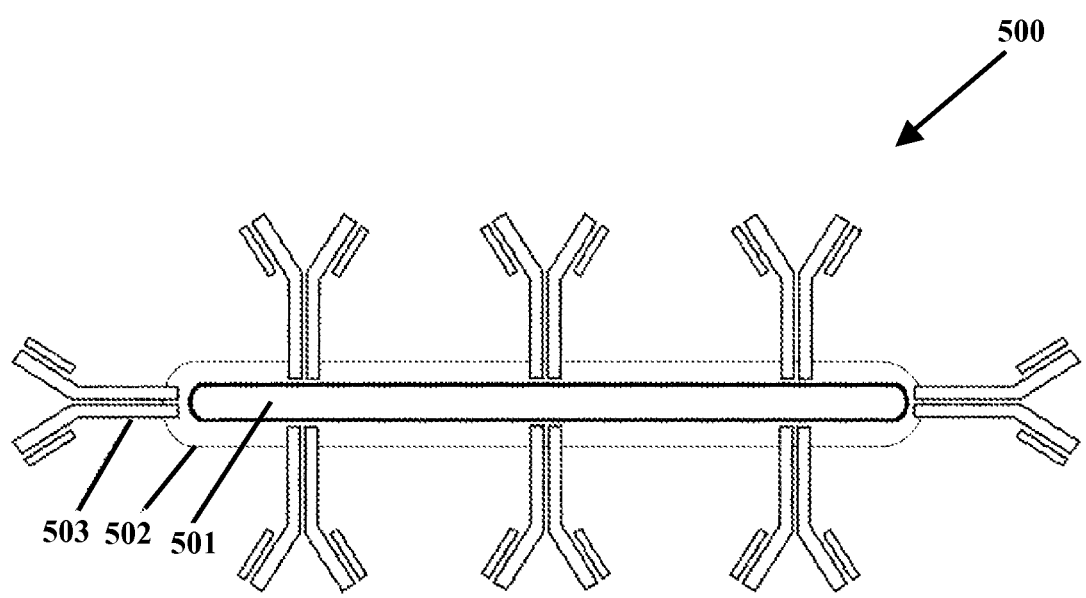
FIG. 6 illustrates a schematic representation of an intrinsic probe used for a treatment of plurality of malignant cells, according to an embodiment herein.

FIG. 6 illustrates a schematic representation of a functionalized intrinsic probe used for the treatment of a plurality of malignant cells, according to an embodiment herein. The intrinsic probe 500 is the smallest entity/particle of nano drug used for the treatment of the malignant cells. The intrinsic probe 500 comprises a metallic nano drug particle 501. The intrinsic probe 500 is functionalized by applying a toxicity shield 502 and a specific connector molecule 503 to the metallic nano drug particle 501. The metallic nano drug particle 501 is a gold particle. Any undesired effect by and to the metallic nano drug 501 is eliminated by providing a coating of toxicity shield 502 made up of Polyethylenegly-col (P.E.G). The specific connector molecule 503 is an antibody such as monoclonal antibodies which are chosen in such a manner so as to enable the intrinsic probe 500 to attach only to the malignant cells. The shape of the metallic nano drug particle 501 is selected from a group consisting of a nano sphere, a nano rod, a nano wire, a nano tube, a nano arc and a nano ring. The intrinsic probe 500 is provided with a metallic nano drug particle 501 so as to induce the magnetic, electrical and thermal/heat effects under the influence of an external magnetic field.

With respect to FIG. 6, no radioactive materials or toxic drugs used. The activity of the nano drug comprising the plurality of intrinsic probe 500 is based on producing the inductive magnetic, electric and thermal fields on the surface of a target cell membrane. The nano scale inductive field causes electric, magnetic and thermal disorders on the surface of the target cell membrane. Any sort of disorder causes a cell dysfunction and death. The nano drug is activated remotely for treating a number of biologic materials/factors including malignant cells. The biologic materials/factors are not only limited to the malignant cells but also include every biological molecules, endogen or exogenous proteins, toxins, viruses, bacteria, abnormal or malignant cells and tissues. The biologic materials/factors are also termed as "targets".

A layer of PEG 502 is coated over the intrinsic probe 500 to reduce the toxicity of metallic nano drug particle 501. There are a number of metallic nano structures which are allowed to be used in the position of gold based nano drug particle 501. Some of the other metallic nano structures are potentially toxic to human tissues. Thus, the toxicity shield 502 is effective for blocking the toxicity of the specific metallic nano particles 501 which are toxic to human tissues and protects the human body from any danger.

According to an embodiment herein, there is a possibility for the intrinsic probe 500 to be attacked by an immune system of a patient before being attached to the malignant cells. The coating of PEG 502 or any similar coating material keeps the intrinsic probes 500 safe from the immune system and increases the efficiency of the nano drug as a whole.

Figure 7:
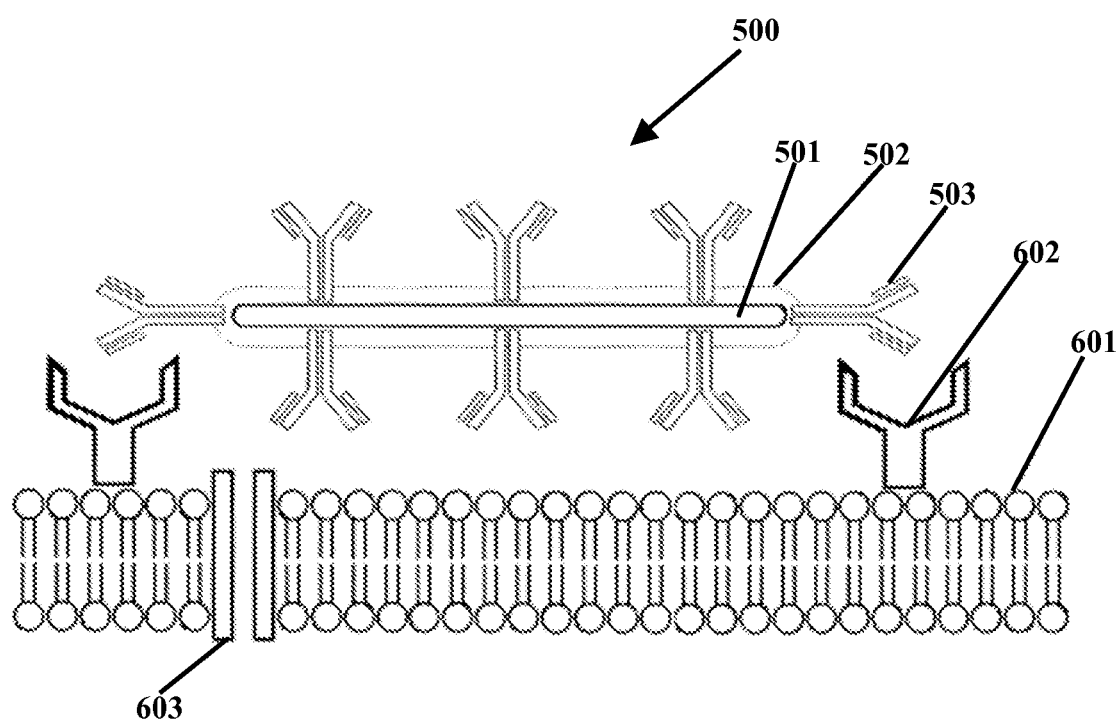
FIG. 7 illustrates a schematic representation of an intrinsic probe comprising a gold nano rod attached to a malignant cell, according to an embodiment herein.

FIG. 7 illustrates a schematic representation of an intrinsic probe comprising a gold nanorod attached to a malignant cell, according to an embodiment herein. With respect to FIG. 6, the intrinsic probe 500 comprises a metallic nano drug particle 501. The intrinsic probe 500 is functionalized by applying a toxicity shield 502 and a specific connector molecule 503 to the metallic nano drug particle 501. A plurality of specific connector molecules 503 is provided on the metallic gold nano particle 501. An intrinsic probe 500 is connected to a cell membrane 601 of a malignant cell through a plurality of cell receptors 602 placed on the cell membrane 601. The cell membrane 601 or plasma membrane is a biological membrane that separates the interior of all the cells from the outside environment. The membrane separates intracellular spaces from each other. The cell membrane 601 is selectively permeable to ions and organic molecules to control the movement of substances in and out of cells through the ion channels 603. The cell membrane comprises a lipid bilayer with embedded proteins. The cell membranes 601 are involved in a variety of cellular most vital processes. The cell membrane 601 is selectively permeable and is able to regulate the entry and exit of the particles in the cell, thereby facilitating the transport of materials needed for survival. A cell is dependent on the cell membrane 601 in some of the most important activities such as absorbing food and oxygen, balancing ions and osmotic pressure, cell signaling and reproduction. Most of the activities have electromagnetic basis and any problem with electromagnetic balance of the cell membrane 601 cause a cell dysfunction or death.

With respect to FIG. 7, cell receptors 603 are molecules which are present on the surface of almost every cell in a human body. The cell receptor 603 molecules help the cell to introduce to the other cells. The cell receptor 603 molecules also help the cells to absorb the required materials from the environment. The cell receptor 603 molecules have the identification function for the cells and act similar to fingerprinting. As well as any other cells in the body, the cell receptors 603 are also present on the surface of respective cytoplasmic membranes in the malignant cells. The intrinsic probe 500 is attached to the malignant cells through the connectors provided between the specific connector molecule 503 and cell receptors 602 respectively.

According to an embodiment herein, the functionalized intrinsic probes are circulated in the body of the patient through the blood stream for attaching with a target. The target is any one of a plasma membrane of a malignant cell, a cell wall of a bacterium, a viral capsid, etc. The embodiments herein are employed for destroying or disabling not only the malignant cells but also any other undesired biologic element inside the body. For example there is a protein cover over every virus called capsid. A capsid is the protein shell of a virus. The capsid is sensitive to temperature and comprises several oligomeric structural subunits made of protein called protomers. Further, the capsid is made of protein and is sensitive to heat and electromagnetic fields. According to an embodiment herein, the capsid is a target for the functionalized nano drug particle. Thus, the method and system of the embodiments herein is able to potentially destroy or disable any virus or bacterium inside a human body.

According to an embodiment herein, the functionalized intrinsic probe comprising gold nano drug particle provides a high radio opacity. When a patient infused with a plurality of intrinsic probes undergoes a medical imaging procedure, the target area attached with the plurality of intrinsic probes is easily detected. Thus, the functionalized intrinsic probe is used as a specific detector.

According to an embodiment herein, the functionalized intrinsic probe induces the electrical, magnetic and thermal effects under the influence of an external magnetic effect produced by the electromagnetic inductor. The intrinsic probes attached to the target alter or disturb the normal electric, magnetic and thermal conditions of the target to cause a dysfunction or destruction of the target.

According to an embodiment herein, the varying magnetic field produced by the electromagnetic inductor is maintained perpendicular and not parallel to the space housing the intrinsic probes. The electromagnetic inductor with U shaped arms produces two magnetic fields which are mutually perpendicular to each other so that even incase of one magnetic field being parallel to the plurality of intrinsic probes, the other magnetic field which is perpendicular to the intrinsic probes activates the intrinsic probes. The two electromagnetic inductors work independently and alternatively. Alternately, the angle between the intrinsic probes and the magnetic field is maintained perpendicular or at some angle by continuously changing the direction of rotation by 90 degrees when a rectangular electromagnetic inductor is used. Further, the electromagnetic inductors create the perpendicular magnetic fields and the power of the magnetic fields change alternatively.

According to an embodiment herein, the body of patient is put under the high frequency magnetic field which produces electric and magnetic field surrounding the intrinsic probe. The magnetic field produced by the electromagnetic inductor provides an unlimited penetration inside the human body. The magnetic field is able to penetrate deep inside every tissue of the body and even inside the bone marrow. Thus, the electromagnetic inductor together with the plurality of intrinsic probes provides a solution for treating the malignant cells optimally at every point in the human body.

According to an embodiment herein, a method to detect and destroy micro-metastasis is provided. A micro metastasis is a process in which the malignant cells spread from the target site to the other healthy tissues and cells. The transferred malignant cells are also too minute/small to be detected. The embodiment herein enables to detect and destroy the malignant clusters/cells which have left the main tumor site and is likely to form a new tumor. The method involves injecting the nano drug comprising a plurality of intrinsic probes to the blood stream of a patient. The injected intrinsic probes are circulated inside the human body through the blood stream and are attached to the malignant cells found in any part of the body. The body of the patient is put inside the electromagnetic inductor. The electromagnetic inductor activates all the intrinsic probes by the process of electromagnetic induction to damage/destroy the malignant cells. All the tumor sites in which the malignant cells are present inside the body either in clustered or individual form, are destroyed. A physician or a specialist doctor is able to treat the patient without knowing the exact site of the micro metastasis. The entire body of the patient is subjected to the magnetic field.

According to an embodiment herein, a method for operating the electromagnetic inductor to treat a cancer patient is provided. The method involves using an electromagnetic inductor. A non-metallic bed for the patient is centrally arranged inside the electromagnetic inductor. The patient is made to lie down on the non-metallic bed and an operator moves the bed inside the electromagnetic inductor. The operator turns ON a laser ray generator and moves the non-metallic bed to keep the body of the patient exactly in an appropriate place as aimed by the laser beam. The appropriate place is the location at which the laser beam is pointed exactly towards the tumor site which is marked by a physician. In the next step, the operator turns ON the electromagnetic inductor and chooses the required power and frequency of the magnetic field that are suggested by the physician. An adjustable frequency inverter is used to provide the high frequency electric current for the electromagnetic inductor. The operator adjusts the frequency with an adjustable frequency inverter. The power of the magnetic field is also adjusted by using an adjustable power generator. The current passing through the coils of the electromagnetic inductor generates heat. A plurality of fans is provided to keep the electromagnetic inductor cool by circulating air continuously.

According to an embodiment herein, a laser ray generator is provided in the electromagnetic inductor. The function of the laser ray generator is to show the operator the exact axis of the magnetic fields produced by the electromagnetic inductor. Once a patient diagnosed with cancerous cells is infused with nano drug particles, the nano drug particles are circulated inside the body and attached to the target cells. A physician diagnoses the exact position of the tumor by using the MRI, X-Ray or any medical imaging procedures. The physician marks the exact position of the target on the body of the patient by using a normal pen or marker. Then, an operator positions the body of the patient in the electromagnetic inductor. The laser beam is projected on the marked target site. The electromagnetic inductor produces magnetic field with dense and parallel lines in the center. The laser ray generator is used only for aiming the position of the target under the high frequency and dense magnetic field produced by the electromagnetic inductor so that high frequency and dense magnetic field produced by the electromagnetic inductor are directed towards or focused on the marked target site illuminated with laser beam.

According to an embodiment herein, a method is provided for infusing the nano drug inside the body of the patient and attaching the nano drug to the target malignant cells. The nano drug comprising intrinsic probes is activated by the high frequent magnetic field which is generated by electromagnetic inductor. The nano drug is slowly injected into the blood vessels and circulated through the blood stream. The nano drugs circulated through the blood stream exit where the blood vessels leak at the site of malignant cells such as cancer tumor. The nano drugs enter into the extracellular fluid. The nano drug comprising a plurality of intrinsic probes is circulated inside the extracellular fluid and attached to respective specific antigens that are found. The intrinsic probes, which are not attached to the tumor cells, are circulated continuously inside the extracellular fluid and are finally collected by the lymph vessels and go to lymph nodes. Afterwards a fluid called lymph is passed through the lymph vessels and circulated back into the blood stream. After a few cycles of nano drug circulation in the blood vessels, extracellular fluid, lymph and blood, the intrinsic probes are attached to the target cells. Once the intrinsic probes are attached to the target cells, the body of the patient is put under the high frequent magnetic field and treated as per the guidance and advice of the physician. In brief, the entire pathway of drug circulation in the body comprises a slow injection of the drug into the blood stream, circulation of the injected drug through the blood vessels, leaking out of drug from the blood vessels to the extracellular fluid, circulation of the drug in the extracellular fluid, collection of the drug circulated through the extra cellular fluid by the lymphatic vessels, circulation of the collected drug in the lymphatic vessels and returning the circulated drug to the blood stream.

According to an embodiment herein, a plurality of nano structures of different materials are used in the place of gold based nano drug particle. The selected nano structure must be a conductor. Also, the factors used for selecting the nano structure used in conjunction with an electromagnetic inductor include but not limited to conductivity, length, width, material surface shape and free electrons on the surface. A general shape such as an elongated shape of the nano conductor is also important but nano structures in other shapes are potentially used in this position. The other shapes of the nano structures in use are spherical, rod, cone, wire, tube, crystal, etc. The shape of the nano structure is selected in such a manner that the shape of the nano conductor is to be able to produce bipolar electric poles during an electromagnetic induction.

Figure 8:
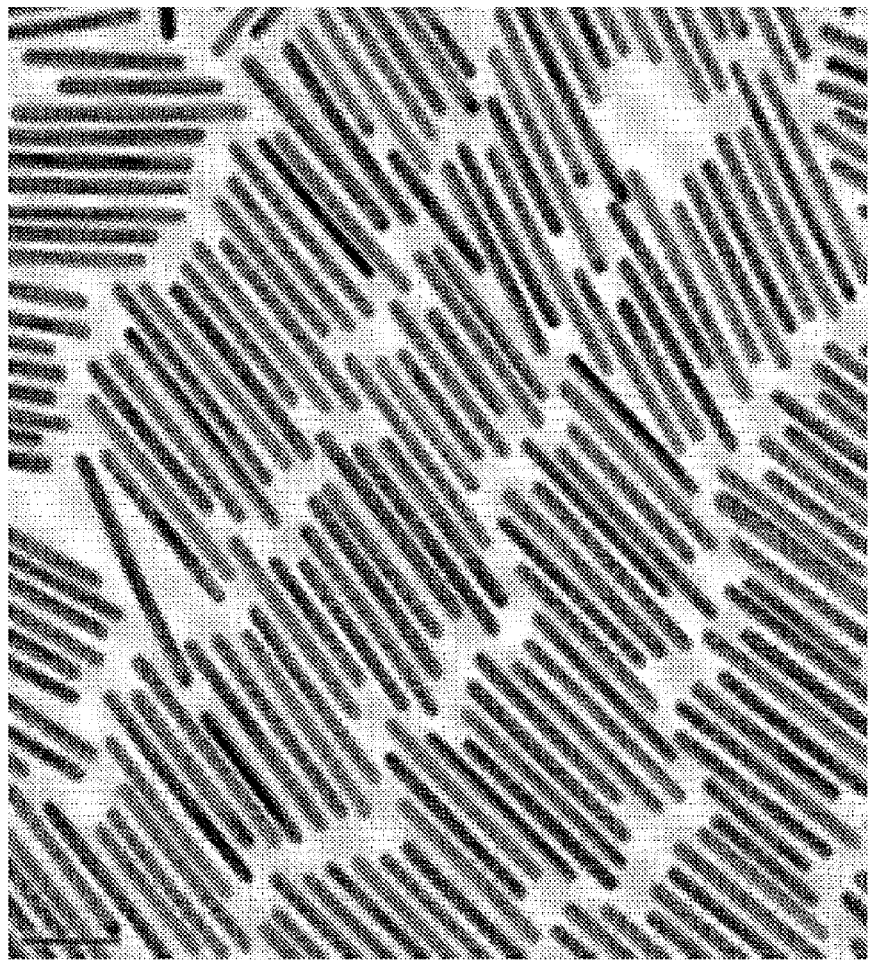
FIG. 8 illustrates an electron microscope image of a plurality of nano rods, according to an embodiment herein.

FIG. 8 illustrates an electron microscope image of a plurality of nano rods, according to an embodiment herein. The nanorods are made from gold material.

Figure 9:
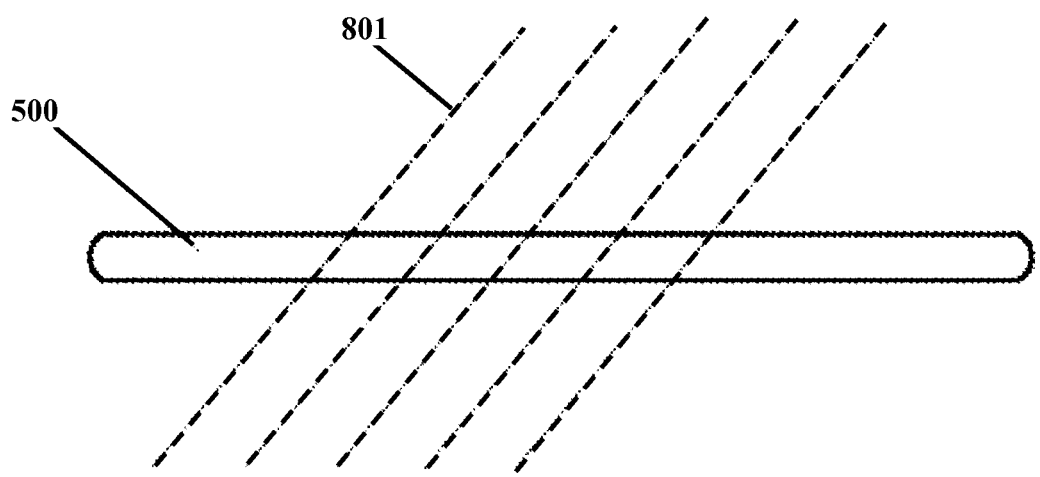
FIG. 9 illustrates a schematic representation of an intrinsic probe under the influence of an alternating magnetic field in one direction, according to an embodiment herein.
Figure 10:
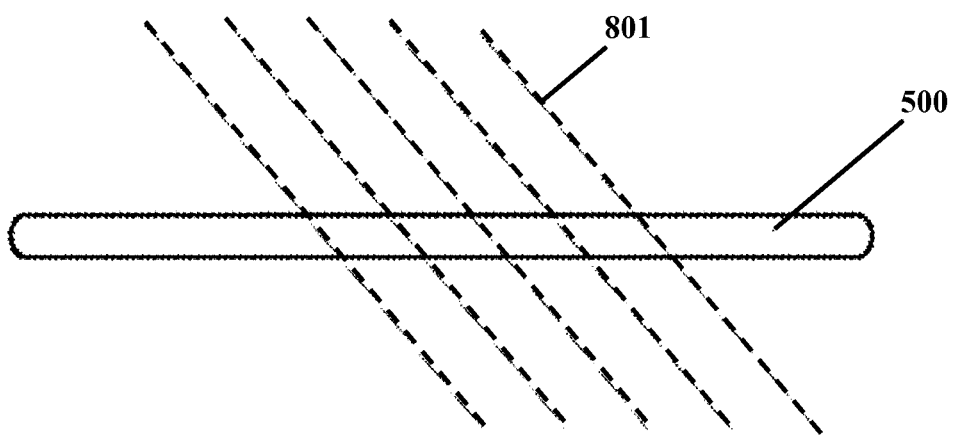
FIG. 10 illustrates a schematic representation of an intrinsic probe under the influence of an alternating magnetic field in another direction, according to an embodiment herein.

FIG. 9 and FIG. 10 illustrate a schematic representation of an intrinsic probe under the influence of alternating magnetic field, according to an embodiment herein. With respect to FIG. 9 and FIG. 10, a current is produced generally in a conductor when the conductor is moved through a magnetic field 801 or when the conductor is placed in a changing magnetic field 801. The magnetic field 801 applies a force on the free electrons inside the conductor and causes the flow of electrons called current. The process of generating current in a conductor by placing the conductor in a changing magnetic field 801 is called induction. The process is called as induction because there is no physical connection between the conductor and the inductor.

According to an embodiment herein, the conductor is a gold nano particle in a predetermined shape and size. The gold nano particle is a part of the intrinsic probe 500. The intrinsic probe 500 comprising gold nano particle in a rod shape is shown. The magnetic field 801 passes through the intrinsic probes 500 at a particular angle thereby inducing a specific electric, magnetic and thermal effect in the intrinsic probe 500. When the magnetic field 801 is perpendicular to the intrinsic probes 500, then a maximum electrical magnetic and thermal effect is induced. When the magnetic field 801 is parallel to the intrinsic probes 500, then minimum effect is induced. Thus an alternating magnetic field 801 with a changing direction is always produced by the electromagnetic inductor to provide a maximum induction effect.

Figure 11:
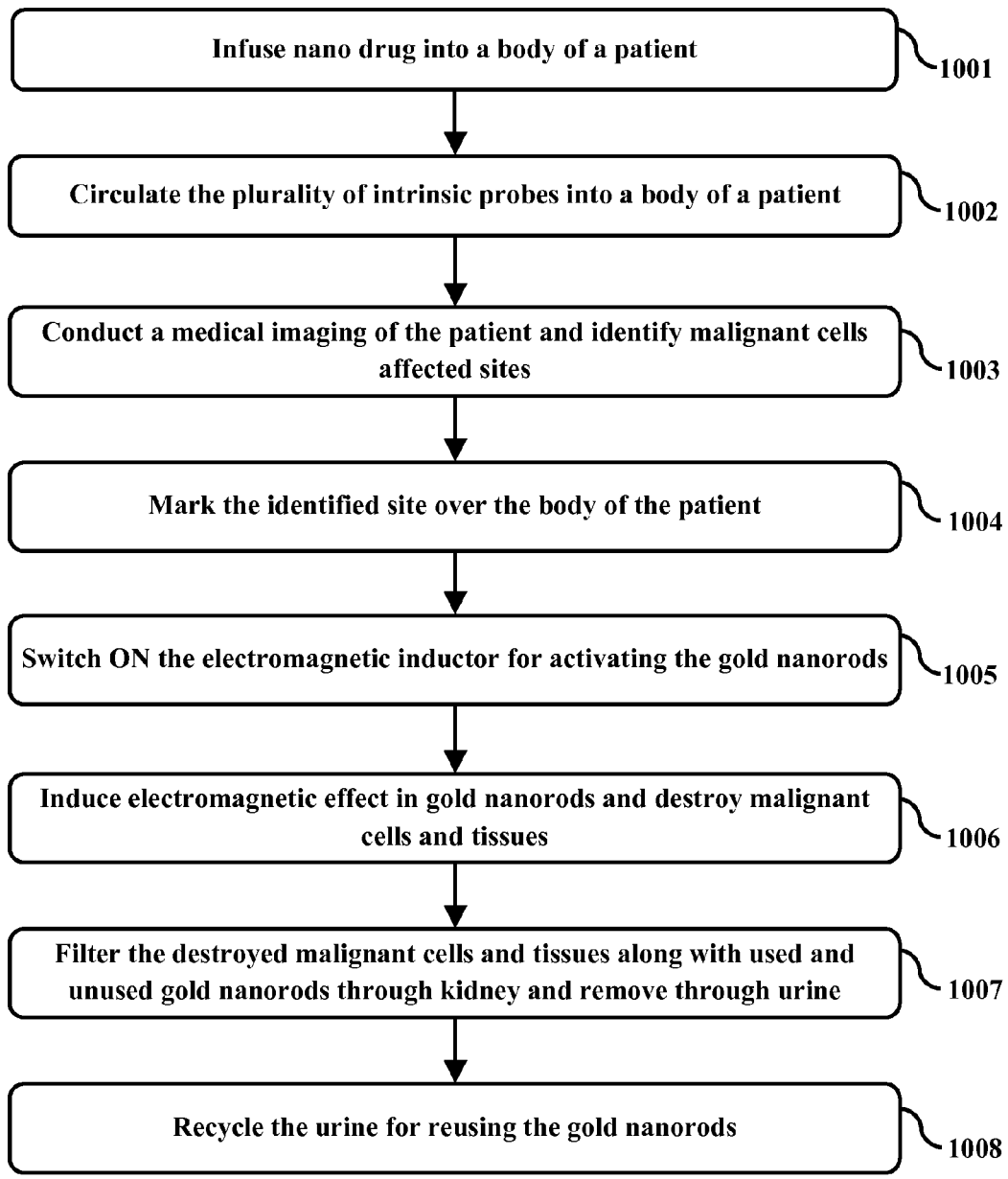
FIG. 11 illustrates a flow chart indicating a method for treating the malignant cells using the electromagnetic inductor and infused intrinsic probes inside the human body, according to an embodiment herein.

FIG. 11 illustrates a flow chart indicating a method for treating the malignant cells using electromagnetic inductor and infused intrinsic probes inside the human body, according to an embodiment herein. An introduction of a substance, such as a fluid, electrolyte, nutrient, or drug, directly into a vein or interstitially by means of a gravity flow is termed as infusion. The nano drug comprising a plurality of intrinsic probes is injected in the blood stream by an intra venous infusion (1001). The infused intrinsic probes comprising gold particle in nano rod shape are circulated all over the body through a blood stream and attached to the target malignant cells. After the infusion of nano drug, the gold nano rods needs time to get attached to the target. The time of attachment is dependent on the characteristics of the target. For example, when the target is a malignant tumor, the attaching time is dependent on the place and size of the tumor and also a type of tumor. The rest of the intrinsic probes which are not attached to targets, are filtered by the kidneys and removed out of the body through urine (1002). After an elapse of a predetermined time, a medical imaging procedure such as an X-ray or MRI or CT scan is carried out to observe and compare the tumor with previously acquired or obtained images. The imaging process provides an advantage during the treatment and in the follow up process after the treatment of the patient. The gold nanorods have high radio opacity in the nano drug thereby enabling to visualize the targets in imaging easily (1003). The doctor locates the target and marks the target on the body of the patient by a normal marker. And then the patient is put inside the inductor (1004). After placing the body of the patient inside the electromagnetic inductor, the power supply is switched ON. The electromagnetic inductor generates high frequency magnetic field and activates the gold nanorods (1005). The gold nanorods which are attached to the targets induce the electric, magnetic and thermal effect under the influence of the high frequency magnetic field to cause a malfunction or destruction of the target. A laser ray generator directs the operator to position the body of the patient at point of maximum magnetic field density. An optimal treatment is provided when the target is positioned in the place located with a projected laser beam, as high frequency magnetic field has maximum density in that area (1006). After the target is destroyed, the waste materials comprising destroyed malignant cells, tissues, used gold nano rods, etc., are filtered by the kidney and removed through the urine (1007). The urine is then recycled to reuse the gold nano rods (1008).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the invention is described with various specific embodiments, it will be obvious for a person skilled in the art to practice the invention with modifications. However, all such modifications are deemed to be within the scope of the claims.

It is also to be understood that the following claims are intended to cover all of the generic and specific features of the present invention described herein and all the statements of the scope of the invention which as a matter of language might be said to fall there between.

What is claimed is:

1. A system for detecting, actively targeting and selectively treating targets in a human body by a non-invasive procedure, the system comprising:
   an electromagnetic inductor for generating a high frequency magnetic field;
   a support post for supporting the electromagnetic inductor at a predetermined height;
   an electromotor for rotating the electromagnetic inductor around an axis at a point of support;
   a non metallic bed for supporting a patient under treatment;
   a head rest provided at one end of the non-metallic bed;
   a bed moving track arranged below the non-metallic bed for adjusting a position of the patient under treatment to a desired position;
   a laser ray generator for indicating a magnetic lines of force and an area in which a magnetic field density or magnetic flux is maximum, and wherein the laser generator enables an operator to aim at a target in a human body of the patient;
   one or more air circulating fans for maintaining the electromagnetic inductor at a normal temperature by a continuous circulation of air;
   wherein the electromagnetic inductor produces electric, magnetic and thermal effects on a probe placed in the target to activate a nano drug, and wherein the nano drug is infused into a blood stream of the patient and attached to a surface of the target to dysfunction or destroy the target, and wherein the target is selected from a group consisting of cells, biological molecules, endogen or exogenous proteins, toxins, viruses, bacteria, abnormal or malignant cells, malignant cell membrane, a bacterial cell wall, a yeast cell wall, a viral capsid and tissues.

2. The system according to claim 1, wherein the probe is a conductive nano drug, comprising:
   a nano conductor, and wherein the nano conductor is formed in a shape of a nano structure, and wherein the nano structure is selected from a group consisting of a nano rod, a nano wire, a nano tube, a nano arc and a nano ring, and wherein the nano structure is a nano rod, and wherein the nano conductor is a metallic nano conductor, and wherein the nano rod is a gold nano rod;
   a toxicity shield, wherein the toxicity shield is formed by coating Poly Ethylene Glycol (PEG) material over the nano conductor for preventing toxic effect of a conductor material or element; and
   a specific connector molecule for attaching the nano conductor to the target in the human body of the patient.

3. The system according to claim 1, wherein, the nano drug comprising the nano conductor is introduced inside a body of the patient by mixing the nano drug in a normal 0.9% NaCl saline solution to obtain a nano drug solution and by infusing the nano drug solution into a vein of the patient, and wherein the nano drug is circulated inside the body of the patient through blood vessels to attach the nano drug to a surface of the targets, and wherein a plurality of unattached nano drugs are expelled from the body of the patient through urine.

4. The system according to claim 1, wherein the electromagnetic inductor produces the high frequency magnetic field across a nano conductor in the nano drug, which is attached to the surface of the targets, and induces magnetic, electric and thermal effects in the nano conductor to activate the nano drug to cause a dysfunction or a destruction of the target, and wherein the nano drug causes a malfunctioning of the target and causes a dysfunction and a destruction of the target.

5. The system according to claim 4, wherein electric, magnetic and thermal effects induced in the nano conductor depends on a size of the nano conductor and a frequency of a magnetic field, and wherein a direction and a magnitude of the magnetic field are changed continuously.

6. The system according to claim 1, the electromagnetic inductor is designed in any one of an open U shape, a closed circular shape, and a rectangular shape, and wherein the electromagnetic inductor produces dense and parallel magnetic lines of force at a centre.

7. The system according to claim 1, wherein a laser beam projected by the laser ray generator is a planar laser beam, and wherein the laser ray generator projects the laser beam at a place with a maximum magnetic flux and wherein the maximum magnetic flux is generated by the electromagnetic inductor due to the high frequency magnetic field, and wherein the movable bed track positions a target area of the patient at the place of maximum magnetic flux indicated by the laser ray generator to provide an optimal treatment.

8. The system according to claim 1, wherein the probe comprising metallic nano conductor has a radio opacity to visualize the target during an imaging process.

9. The system according to claim 1, wherein the probe is activated remotely, and wherein the intrinsic probe is activated to present an electric field and a bipolar magnetic field in a nano scale.

* * * * *